United States Patent
Roelfsema et al.

(10) Patent No.: US 12,214,186 B2
(45) Date of Patent: Feb. 4, 2025

(54) NEUROPROSTHETIC SYSTEM AND METHOD FOR SUBSTITUTING A SENSORY MODALITY OF A MAMMAL BY HIGH-DENSITY ELECTRICAL STIMULATION OF A REGION OF THE CEREBRAL CORTEX

(71) Applicant: NEDERLANDS HERSENINSTITUUT, Amsterdam (NL)

(72) Inventors: Pieter R. Roelfsema, Amsterdam (NL); Xing Chen, Amsterdam (NL)

(73) Assignee: NEDERLANDS HERSENINSTITUUT, Amsterdam (NL)

( * ) Notice: Subject to any disclaimer, the term of this patent is extended or adjusted under 35 U.S.C. 154(b) by 152 days.

(21) Appl. No.: 17/271,039

(22) PCT Filed: Aug. 28, 2019

(86) PCT No.: PCT/EP2019/072997
§ 371 (c)(1),
(2) Date: Feb. 24, 2021

(87) PCT Pub. No.: WO2020/043790
PCT Pub. Date: Mar. 5, 2020

(65) Prior Publication Data
US 2021/0308448 A1    Oct. 7, 2021

(30) Foreign Application Priority Data

Aug. 31, 2018 (EP) .................................. 18192027
Oct. 1, 2018 (EP) .................................. 18197958

(51) Int. Cl.
*A61N 1/00* (2006.01)
*A61N 1/05* (2006.01)
(Continued)

(52) U.S. Cl.
CPC ....... *A61N 1/0531* (2013.01); *A61N 1/36046* (2013.01); *A61N 1/36103* (2013.01); *A61N 1/36135* (2013.01); *A61N 1/37514* (2017.08)

(58) Field of Classification Search
None
See application file for complete search history.

(56) References Cited

U.S. PATENT DOCUMENTS

| 5,361,760 A | 11/1994 | Normann et al. |
| 8,560,041 B2 * | 10/2013 | Flaherty ................ A61B 5/685 601/1 |

(Continued)

FOREIGN PATENT DOCUMENTS

| CN | 1973918 A | 4/2010 |
| WO | 2008109298 A2 | 9/2008 |
| WO | 2016126340 A2 | 8/2016 |

OTHER PUBLICATIONS

Horne, L., Alvarez, J., Mccarthy, C., Salzmann, M., & Barnes, N. (2016). Semantic labeling for Prosthetic Vision. Computer Vision and Image Understanding, 149, 113-125. https://doi.org/10.1016/j.cviu.2016.02.015 (Year: 2016).*
International Search Report dated Dec. 11, 2019 for PCT/EP2019/072997.

*Primary Examiner* — John R Downey
*Assistant Examiner* — Anant A Gupta
(74) *Attorney, Agent, or Firm* — Suiter Swantz IP

(57) ABSTRACT

A neuroprosthetic system for substituting a sensory modality of a mammal by electrical stimulation of a region of the cerebral cortex corresponding to the neural modality to be substituted. The system includes at least one sensor for generating a sensed data feed by sensing a neural modality to be substituted, an electrode unit including a plurality of three-dimensional arrays of flexible electrode shafts for implantation of a region of the cerebral cortex, a rigid electrode support structure for guiding the flexible electrode (Continued)

shafts into the region of the cerebral cortex and for retraction after implantation, a driving unit for electrically driving the electrode, a recording unit, and a processing unit for analysing sensed data feed for providing stimulation patterns for electrically driving groups of electrical contacts of the electrode unit corresponding to subsets of locations in the region of the cerebral cortex, for substituting the sensory modality.

9 Claims, 4 Drawing Sheets

(51) Int. Cl.
*A61N 1/36* (2006.01)
*A61N 1/375* (2006.01)

(56) References Cited

U.S. PATENT DOCUMENTS

| | | | |
|---|---|---|---|
| 10,492,702 B2 * | 12/2019 | Chang | A61B 5/377 |
| 2002/0091421 A1 * | 7/2002 | Greenberg | A61N 1/36046 |
| | | | 607/54 |
| 2006/0106432 A1 * | 5/2006 | Sawan | A61N 1/0551 |
| | | | 607/54 |
| 2008/0208283 A1 * | 8/2008 | Vetter | B29C 45/14639 |
| | | | 607/45 |
| 2010/0094382 A1 | 4/2010 | Pezaris et al. | |
| 2014/0222103 A1 | 8/2014 | Lauritzen et al. | |
| 2016/0331968 A1 * | 11/2016 | Greenberg | A61B 5/24 |
| 2017/0079770 A1 | 3/2017 | Li | |
| 2018/0104487 A1 | 4/2018 | Greenberg et al. | |
| 2021/0365114 A1 * | 11/2021 | Hewage | G06N 20/00 |

\* cited by examiner ns, by a relatively
NEUROPROSTHETIC SYSTEM AND METHOD FOR SUBSTITUTING A SENSORY MODALITY OF A MAMMAL BY HIGH-DENSITY ELECTRICAL STIMULATION OF A REGION OF THE CEREBRAL CORTEX A neuroprosthetic system and method for substituting a sensory modality of a mammal by high-density electrical stimulation of a region of the cerebral cortex.

TECHNICAL FIELD

The present disclosure relates to the field of biomedical engineering and, in particular, to a neuroprosthetics system and method for substituting or inducing a missing or impaired sensory functionality of a mammal, by electrical stimulation of intracortical electrodes, for example to restore functional vision of a human being suffering from partial or total blindness.

BACKGROUND

Neuroprosthetics or neural prosthetics, is a technical discipline related to neuroscience and biomedical engineering concerned with the development of neural prostheses. A neural sensory prosthesis, in its most general form, is a device or system designed to substitute or induce, by neural stimulation in a respective region of the cerebral cortex of a mammal, a sensory functionality, such as visual, auditory, tactile, or olfactory functionality, that might have been damaged as a result of an injury or a disease.

In the field of sensory restoration of visual functionality, for example, damages in the visual system can be generally classified into two groups, i.e. a first group with damage in the visual processing pathway up to and including the ganglion cell layer in the retina, and a second group with damage after this processing stage impairing information flow between the retina and the visual cortex.

For the first group of patients, significant progress has been made towards solutions in the form of retinal prostheses for implantation in the retina, providing low vision to mammals, in which the retinal ganglion cells that connect the eye to the brain have been spared. Retinal implants cannot be used for people with extensive damage to the ganglion cells and/or optic nerve.

For the large group of patients whose sight cannot be restored in the retina, i.e. the above-mentioned second group, prostheses comprised of surface stimulation electrodes for application over the exterior surface of the visual cortex have been developed, as well as prosthesis comprising intracortical electrodes for activation of a sparse subset of phosphene locations in the visual cortex.

US patent application 2010/0094382 discloses a visual prosthesis system operative to deliver electrical signals to the lateral geniculate nucleus of the thalamus of a mammal, which is the part of the thalamus that relays visual information from the eye to the cerebral cortex. The system comprises an array of rigid electrodes, a visual information translator operatively connected to the electrodes, and a visual sensor operatively connected to the array of electrodes. The visual translator is arranged for translating the visual information provided by the visual sensor for stimulating the lateral geniculate nucleus with an electrical signal through the electrodes in a manner to stimulate a subject's brain activity to recognize visual information.

International patent application WO2008/109298 discloses an electrode array for deep brain stimulation, having a plurality of electrode sites or electrical contacts arranged both circumferentially and axially along an elongated carrier. The carrier has a diameter in the range of 1 mm. For implanting an electrode array, an implanting chamber is provided, that is to be attached to the scull of a mammal, and from which a limited number of guide tubes extend for guiding an electrode array for implanting thereof in the brain.

Present neural prosthesis for intracortical stimulation of a mammal only allow for stimulation of a relatively sparse set of neural locations in the brain of a mammal, by a relatively small number of implanted electrodes. Accordingly, a missing or impaired sensory functionality can only be substituted or induced in a very rudimentary manner which, in practice, is not sufficient to allow human beings to regain the missing functionality in a manner for a substantial enhancement of functionally, which would improve their independence and quality of life.

Accordingly, there is a need for an improved neuroprosthetic system and method for substituting a sensory modality of a mammal by electrical stimulation of a respective region of the cerebral cortex of the mammal.

SUMMARY

The above mentioned and other objects are achieved, in a first aspect of the present disclosure, by a neuroprosthetic system for substituting a sensory modality of a mammal by electrical stimulation of a region of the cerebral cortex of said mammal corresponding to said neural modality to be substituted, said system comprising:
  at least one sensor, for use by said mammal, arranged for generating a sensed data feed by sensing a neural modality to be substituted;
  an electrode unit, comprised of a plurality of three-dimensional arrays of flexible, elongated electrode shafts, arranged for intracortical implantation for a dense occupation of such region of the cerebral cortex of said mammal arranged for providing functional coverage of the sensory modality, each shaft comprising multiple electrical contacts, for electrical stimulation of subsets of locations in said region of the cerebral cortex;
  a rigid electrode support structure, arranged for simultaneously guiding said flexible electrode shafts of an array into said region of the cerebral cortex of said mammal during intracortical implantation, and for retracting said support structure after implantation of an array of flexible electrode shafts;
  a driving unit, arranged for electrically driving said electrode unit for stimulating said subsets of locations in said region of the cerebral cortex,
  a recording unit, arranged obtaining neural recording through said electrode unit in said region of the cerebral cortex;
  a processing unit, arranged for analysing said sensed data feed for providing stimulation patterns for electrically driving groups of electrical contacts of said electrode unit corresponding to subsets of locations in said region of the cerebral cortex, for substituting said sensory modality.

The present disclosure is based on the insight that a functional substitution of an impaired neural modality necessitates electrical stimulation of dense locations in a respective region of the cerebral cortex providing functional coverage of the sensory modality.

Some regions of the cerebral cortex have complex shapes. The visual region V1, for example, has a folded structure. The disclosure is based on the insight that through over-dimensioning of the electrodes dense coverage of these regions can be achieved. Although some electrodes may actually fall outside of this region of interest, e.g. visual region V1, still a large number of electrodes covered this region in such a sufficient dense manner that the sensory modality can be substituted in a functional manner.

The term functional manner refers to at least such restoration of the sensory modality to a level sufficient for the patient to improve their independence and quality of life. This would not necessarily require full restoration of the sensory modality but at least such restoration beyond basis functioning in which only proof-of-concept is achieved.

This is achieved, by the present disclosure, in providing plural three-dimensional arrays of flexible electrode shafts and a rigid electrode support structure, arranged for inserting in a simulations manner (i.e. in one single step in which all electrode shafts of one array are displaced together instead of one-by-one) all flexible electrode shafts of an array into a target region of the cerebral cortex of the mammal, and for retracting the support structure after implantation of the flexible electrode shafts.

In this way, a dense set of very thin flexible electrode shafts for uniform stimulation of locations in the cortex can be applied, in particular in cortical areas that are otherwise difficult to access, such as in a sulcus of the cerebral cortex. In this way, these areas have such a dense distribution of electrodes in said area of the cerebral cortex of the patient or mammal that functional coverage of the sensory modality is achieved.

High-density stimulation of the cortex provides a functional substitution of the missing neural modality, that is to restore for example vision in a meaningful manner providing functional coverage.

The term three-dimensional array refers to the fact that the electrical contacts for stimulation and/or reception of stimuli occupy a three-dimensional volume or region.

The term functional sensory primitives refers to basic neural stimulations by which a basic substitution of the missing sensory modality can be provided to the mammal.

In an particular embodiment of the present disclosure, for restoring vision, the neuroprosthetic system is arranged for substituting visual perception in a visual region of said cerebral cortex of said mammal, wherein said at least one sensor comprises at least one portable imaging unit arranged for capturing images and generating a captured image data feed, wherein said driving unit is arranged for evoking phosphenes at locations in said visual region of the cerebral cortex, and wherein said processing unit is arranged for providing said stimulation patterns for stimulating groups of electrical contacts of said electrode unit corresponding to subsets of phosphene locations in said visual region of the cerebral cortex for evoking phosphenes for substituting said visual perception comprised of phosphene patterns obtained through semantic segmentation of images of said captured image data feed.

Semantic segmentation of the images provides for a patterned stimulation of the visual cortex, and may comprise semantic segmentation, applying Convolutional Neural Networks (CNNs), for example, for activating the appropriate phosphenes and to thereby solve various visual recognition problems, such as image classification, object detection, and action recognition.

The term semantic segmentation refers to the task of processing images in which each pixel of the image is assigned with a class which may refer to objects, persons, etc. With semantic segmentation, the coarse image information is translated into fine inference such that every pixel is labelled or classified with a class of the enclosing object, region or area. Whereas the input of the semantic segmentation could be raw image data, the output may be translated into regions or structures that allow the user to identify and localize primitive and more complex shapes, line segments, curve segments, etc.

Whereas semantic segmentation may refer in particular to translation of images in said sensed data feed, other segmentation or classification processes may be applicable for non-visual senses. For example, for auditory substitution, similar translation processes may apply in which the relevant sound features of more complex sounds are provided to the patient.

The imaging system may comprise any of a digital camera or cameras, photodetectors or photosensors, for operating in the visual and/or InfraRed, IR, spectrum, and mounted at glasses or the like.

It is noted that in auditory substitution, for example, sensory primitives may be comprised of a set of basic tones or frequencies, whether or not limited to a particular frequency band, such as a telephone frequency band for substituting speech, for example, and vowel and consonant sounds that form the sound of words characteristic of a language. The sensor or sensors generating the data feed may be comprised of one or a plurality of sound sensors, such as voice sensitive microphones in the case of substituting speech.

Sensory receptors are found all over the body including the skin, epithelial tissues, muscles, tendons and joints. Sensory primitives in the case of tactile restoration may include somesthetic senses, i.e. the sense of touch, proprioception (sense of position and movement), and haptic perception. The mapping of the body surfaces in the brain is called somatotopy. In the cortex, it is also referred to as the cortical homunculus. For restoration of touch, for example, pressure sensors may be applied.

In an embodiment of the present disclosure, the system comprises a switching device for channelling one or more stimulation signals of said driving unit to subsets of electrical contacts located within in said region of the cerebral cortex providing said functional coverage of the sensory modality.

The switching device enables the system to connect multiple (groups) of electrode shafts or particular electrical contacts thereof to one single signal generator. As such, it is not necessary to have a signal generator for each electrical contact, and only a significant lower amount required which preferably corresponds to the number of different stimulation signals the driving unit is required to generate.

In an embodiment of the present disclosure, each of the multiple three-dimensional arrays of flexible electrode shafts is comprised of a base plate, and the flexible electrode shafts extend from one surface of the base plate, wherein the electrical contacts are distributed in the lengthwise direction of the elongated electrode shafts, and wherein each electrical contact connects to an electrical lead supported by the base plate.

The base plate provides the necessary support for the electrical wiring to each of the electrical contacts of the electrodes. As the electrodes are attached to the base plate, the electrical leads can be provided using printing or etching techniques or the like, available from semiconductor engineering.

In a practical embodiment, in particular for use with human beings, the base plate has a substantially quadrangular shape, having side dimensions in the range of 4-30 mm, and more preferably between 8 and 12 mm, and a thickness in the range of 10-200 μm, the flexible electrode shafts are ribbon shaped, having a length in the range of 0.5-40 mm, more preferably between 4-40 mm, a width in the range of 5-100 μm, more preferably between 10-100 μm, and a thickness in the range of 1-30 μm, more preferably between 1-15 μm, wherein the electrical contacts are distributed in lengthwise direction of the electrode shaft with a mutual maximal spacing of 800 μm, in particular a mutual spacing of 40 μm, and wherein the electrode shafts extend from the base plate with a mutual spacing in the range of 0.1-2 mm, more preferably between 0.4-1 mm.

Electrodes having dimensions disclosed above are long enough to be inserted next to the calcarine sulcus, which contains a large fraction of the visual field representation. Studies demonstrated that these electrodes reliably detect the activity of individual neurons. Importantly, they do not appear to cause neuronal degradation or glial scar formation.

In an embodiment of the neuroprosthetic system according to the present disclosure, the electrode support structure comprises a plurality of mutually coupled elongated rigid insert shafts (also known as shanks), for guiding said flexible electrode shafts for intracortical insertion in said selected region of the cerebral cortex, said base plate comprising a two-dimensional array of through holes receiving said plurality of insert shafts.

The rigidity of the shafts or shanks is dimensioned such, that the all the electrodes of an array can be positioned at once, for example by hand force, and such that the shafts or shanks are deflectable when experiencing resistance during insertion, for example caused by a blood vessel or the like. In that case, a shaft or shank of the electrode support structure should follow a trajectory avoiding insertion in the blood vessel.

For further enhance inserting the shafts and electrodes, the deflective properties of the shaft and electrode are further improved, in another embodiment of the present disclosure, in that at least one of the insert shafts and the flexible electrode shafts comprise a tapered free end.

In a practical embodiment, for use with the electrode array particularly dimensioned for use in the human brain, the rigid support shafts of the electrode support structure are ribbon shaped, have a length in the range of 0.5-40 mm, more preferably between 4-40 mm, and have a rectangular cross section with a width at least approximately identical to the electrode shaft and a thickness in the range of 10-50 μm, or a cross-section, which is preferably circular, with a diameter of 1-50 μm, more preferably between 10-50 μm, wherein the support shafts are arranged with a mutual spacing in the range of 0.1-2 mm, more preferably between 0.4-1 mm.

With an electrode array of the above dimensions between about 2,500-50,000 electrical contacts per array may be provided.

In an embodiment, a flexible electrode shaft can either be affixed to a respective insert shaft by a brain fluid dissolvable adhesive. That is, after insertion of the electrodes, the adhesive has to quickly dissolve, for safe retraction of the electrode support or by inserting the insert shaft into a hole in the flexible electrode shaft.

In an embodiment of the neuroprosthetic system according to the present disclosure, the said flexible electrode shaft is comprised of a tissue-biocompatible material, such as polyimide or SU-8, said electrical contacts with the brain are comprised of iridium oxide, microstructured platinum or titanium nitride, said base plate is comprised of silicon sheet material, said electrical wires are comprised of electrical conductive materials such as gold, or silicon, said insert shafts are comprised of tungsten or silicon, and wherein said dissolvable adhesive is comprised of polyethylene glycol.

Polyethylene glycol dissolves, for example, after 10-15 seconds after same has come into contact with brain fluid. In this way, a plurality of electrode arrays, say 5-20 arrays, can be relatively quickly implanted, thereby significantly reducing the burden on the patient and surgeon.

Data transfer in the neuroprosthetic system, in a further embodiment of the present disclosure, is provided in that the processing unit comprises a transceiver arranged for wireless data communication, the system comprising a signal transducer arrangement arranged for wireless data communication with the processing unit, the signal transducer arrangement being arranged for controlling the driving unit for driving the electrical contacts in a calibration mode and an operational mode, and wherein the signal transducer arrangement in the calibration mode controls the driving unit to drive the electrical contacts for one of signal stimulation and signal reception by the recording unit.

Operation of the driving unit in an operational and calibration mode is advantageous, in that due to the large amount of electrical contacts, for example between 20,000-500,000 when implanting 5-20 arrays in a region of the cerebral cortex, the calibration mode for determining suitable stimulation strength can be performed separately from the operational mode, for example at night when a patient sleeps.

To this end, in another embodiment of the neuroprosthetic system according to the present disclosure, the signal transducer arrangement is arranged for controlling the driving unit in a calibration mode, for driving the electrical contacts for signal stimulation in a primary cortex area and/or a higher cortical area, and signal reception in the primary cortex area and/or a higher cortical area for determining the strength of the stimulation in the region of the cerebral cortex for substituting the neural modality.

In this manner, the electrode unit can be conveniently calibrated to determine the current and voltage amplitude or intensity, pulse shape, frequency and other stimulation parameters, as well as to determine those electrical contacts of the electrode unit that contribute to the substitution of the missing neural modality. In this way failures or disturbances in the implanted electrodes can be detected and such electrodes or electrical contacts can be excluded from being powered by the driving unit.

Patterned stimulation of locations in the visual cortex area, for example, where stimulation evokes phosphenes, and monitoring corresponding activity in another cortical area allows to predict whether the mammal will be able to perceive an electrical stimulus applied to the cortical visual area. This without any further active interaction of the mammal.

Signal reception from locations in the sensory cortex area, for example, to extract correlations between the neural signals from the electrodes, and use the correlation structure to deduce functional maps of sensory cortex, allows to predict the locations at which the mammal will be able to perceive an electrical stimulus applied to the cortical area.

Operating the signal transducer arrangement for controlling the driving unit in the calibration mode, for driving the electrical contacts in one of signal stimulation and signal reception at predetermined regular time intervals, in accordance with another embodiment of the present disclosure, provides for recalibration of at least one of stimulation signals and potential locations in said region of the cerebral cortex for substituting said neural modality.

It has been observed that over time, the intensity of particular stimulus needs to be adapted, i.e. increased or prolonged, in order to evoke a respective perceptible neural stimulation. This, among others, due to gliosis, degradation of the electrode contact or insulation. In a most severe case, stimulation of a particular position in the cortex may not evoke any neural action anymore. In that case, because of the vast number of stimulation positions available with the electrode unit according to the present disclosure, new subsets of locations in the region of the cerebral cortex for substituting a respective neural modality may be utilized.

For reducing the dimensions of the transducer and driver arrangements, in a further embodiment the signal transducer arrangement comprises electrical simulation circuitry designed for simultaneously energizing, during the operational mode, a plurality of electrical contacts corresponding to a reduced yet functional number of locations for substituting the neural modality in accordance with the sensory primitives.

That is, the capacity of the transducer arrangement and the driver may be effectively limited to the relevant subset of locations that have to be stimulated. Thereby not only reducing the dimensions and costs of the system, but also heat production which has to be observed when applying the transducer and driver arrangement under the skin or under the skull of a mammal.

For efficiently handling large numbers of lead wiring, in an embodiment of the neuroprosthetic system according to the present disclosure, each of the multiple electrical contacts connects by an electrical lead to a plurality of multiplexers and switching circuitry of the transducer arrangement. In addition, or as an alternative, each of the plurality of arrays of flexible electrode shafts may comprise at least one multiplexer and switching circuitry connected to the multiple electrical contacts of the array and one or more multiplexer leads for electrically driving the electrical contacts by the driving unit or for neural recording through the electrical contacts by the recording unit. By the flexible switching circuitry, the electrodes can be electrically stimulated or recorded by amplifiers that are connected to the recording unit.

Implementing a multiplexer and switching circuitry at the support plate of an electrode array significantly reduces the number of leads that have to be guided through the skull to external equipment.

For analysing a sensed data feed for providing stimulation patterns, the processing unit may be arranged for using any one or more of convolutional neural networks, deep networks for semantic segmentation and conditional random fields, for example.

The functionality of the substituted neural modality with the neuroprosthetic system according to the present disclosure may be enhanced or enriched using at least one further sensor, arranged for sensing perceptual information for augmenting the substitution of the neural modality.

An example of such a further sensor, in particular for use with a visual restoration or substitution system, is a so-called eye-tracking sensor or gaze tracking sensor, which may useful for directing the imaging unit based on a subject's gaze. Sound sensors may provide information as to the direction and speed of traffic, for example, augmenting a visual substitution of human being when travelling, for example. The information provided by such a further sensor may be provided directly to the user or indirectly processed through the processing unit and used for determining a subset of locations to be stimulated.

Those skilled in the art will appreciate that other sensors for augmenting the functionality of a neural modality can be provided, such as speed sensors, temperature sensors, tactile sensors, etc.

In a second aspect, the present disclosure provides a rigid electrode support structure for guiding flexible elongated electrodes of an array of electrodes of a neuroprosthetic system, as disclosed above with respect to the first aspect.

In third aspect, the present disclosure provides a three-dimensional array of flexible, elongated electrodes, arranged for intracortical implantation in a region of the cerebral cortex of a mammal, wherein each electrode comprises multiple electrical contacts, for electrical stimulation of dense subsets of locations in said region of the cerebral cortex, in accordance with the first aspect as disclosed above.

In fourth aspect, there is provided an assembly of a three-dimensional array of flexible, elongated electrodes and a rigid electrode support structure as disclosed above, wherein the electrodes and support structure connect by a brain fluid dissolvable adhesive, in accordance with the present disclosure.

In a fifth aspect there is provided a computer program product comprising a data storage device storing computer program code data arranged for analysing a sensed data feed of a neuroprosthetic system according to the first aspect of the present disclosure, for providing stimulation patterns for electrically driving electrical contacts of an electrode unit corresponding to subsets of locations in a region of the cerebral cortex for substituting a neural modality comprised of sensory primitives, when said program code data are loaded into a memory of an electronic processing unit and are executed by said electronic processing unit.

In practice, intracortical implantation in a region of the cerebral cortex of a mammal of a three-dimensional array of flexible, elongated electrodes of said neuroprosthetic system disclosed above, may comprise the steps of:

providing the three-dimensional array of flexible, elongated electrodes, extending from one surface of a base plate comprising a two-dimensional array of through-holes;

providing the rigid electrode support structure for guiding said flexible elongated electrodes of said array into said region of the cerebral cortex, the support structure comprising a plurality of mutually coupled elongated rigid insert shafts;

receiving each of the insert shafts in a respective through-hole of the base plate;

fixing each of said flexible, elongated electrodes to a respective insert shaft, for example by a brain fluid dissolvable adhesive or by a hole at a free end of said flexible electrodes shaft that is engages with a tip of said insert shaft;

implanting said rigid electrode support structure with said affixed three-dimensional array into said region of the cerebral cortex of said mammal, and retracting said rigid electrode support structure from said region of the cerebral cortex of said mammal after said adhesive is dissolved.

The abovementioned and other aspects of the present disclosure will be apparent from and elucidated with reference to the embodiments described hereinafter.

DETAILED DESCRIPTION

Figure 1:
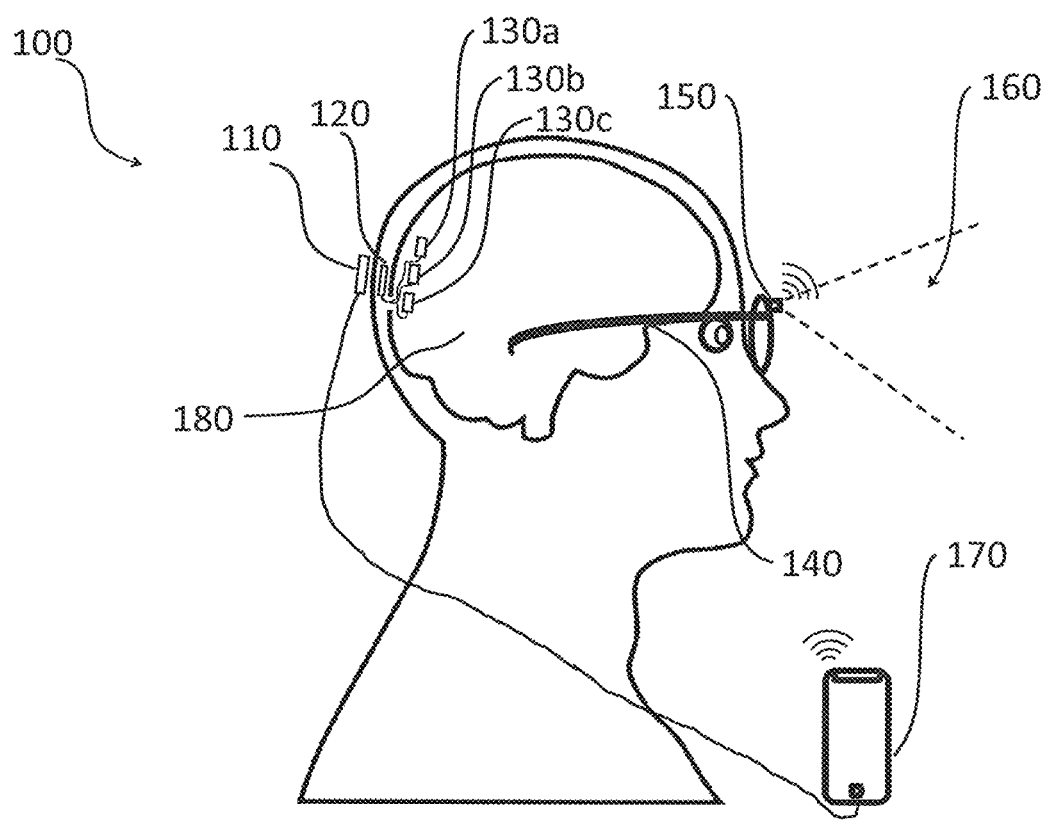
FIG. 1 illustrates, schematically, a neuroprosthetic system according to the present disclosure.

FIG. 1 schematically illustrates a neuroprosthetic system 100 for substituting a sensory modality of a mammal, in this case a patient, by electrical stimulation of a region of the cerebral cortex of the patent which corresponds to the neural modality that is to substituted.

Although the examples illustrated in the figures and described in the description below are directed to a visual neuroprosthetic system in which visual perception is substituted in the visual region of the cerebral cortex, the present invention is not particularly limited solely to the visual sensory modality. The skilled person will appreciate that the present invention is also applicable for other sensory modalities such as the auditory or somatosensory modality.

Merely as in illustration, the system 100 as demonstrated in FIG. 1, contains several separate physical units, which are contained in separate housings. The skilled person will appreciate that some units however, may also be combined into a single housing.

The system 100 at least consists of a sensor 150. The sensor may comprise a digital camera or cameras, photodetectors or photosensors, for operating in the visual and/or InfraRed, IR, spectrum, and mounted at glasses or the like. In the example shown in FIG. 1 the sensor is an image sensor which is mounted on glasses 140 of the patient. The sensor may however also be a separate camera that is attachable to the body or can be worn by patient in any other way. The camera may also be a separate hand held camera unit or incorporated in a portable device such as a mobile phone or portable computer device like a tablet.

The camera 150 is pointed in a direction that corresponds to the field of view 160 of the patient. As such, the camera is able to record or capture a data stream, in this example a data stream consisting of a plurality of images. The data stream contains data or images that cover at least most of the field of view 160. The term field of view refers to the restriction of what is actually visible by the camera 150. Since the human eye may have a larger field of view than most camera devices, the system may also comprise an eye-tracking unit, which is not shown in FIG. 1. The eye-tracking unit is able to detect the position of the eye of the patient, and thus where the eye is directed to. In this way, the camera device may be focused to his direction and generate a data stream that corresponds to the focus area in the field of view of the patient.

The system 100 also consists of an electrode unit 130. The electrode unit 130, in practice, consists of multiple three-dimensional arrays 130a, 130b, 130c. The system 100 consists preferably of approximately 20 of these arrays 130, for example 10 implanted into the left hemisphere and 10 in the right hemisphere.

Each three-dimensional array 130a, 130b, 130c consists of multiple flexible, elongated electrode shafts. These electrode shafts have a shape and are made of a material that makes them suitable for intracortical implantation in the brain 180 of the patient. To make them suitable, these electrode shafts may be manufactured of a tissue-biocompatible material such as a polyimide or SU8. The skilled person will however appreciate that other biocompatible insulating materials in combination with electrical conductive materials may also be suitable.

The electrode shafts are distributed in such a three-dimensional manner over the array that they are able to make electrical contact with a large three-dimensional region of the cerebral cortex, i.e. with most of, or approximately all of the visual region of the cerebral cortex of the patient. This means, that not only in two directions the spacing dl in FIG. 2 between the individual electrode shafts is small, e.g. up 0.4 to 1 mm, but that the electrodes shafts are also longer then electrodes of known electrode arrays, with a length up to 20 or even 40 mm. Preferably, the length of the electrode shafts are in the range of at least 2 to 5 mm till 20 or 40 mm. More preferably, the length is in the range of 5 till 30 mm, even more preferably in the range of 7 till 25 mm, and most preferably in the range of 15 till 20 mm. This way, the electrodes are able to extend beyond a single, or cover even plural folded gyrus in the cerebral cortex.

Each electrode shaft consists of multiple electrical contacts. These contacts may be controlled individually such that some of the contacts of a single electrode shaft are electrically driven or activated by applying a stimulation signal, and others are not operated. Each contact may also be operated for either signal stimulation or signal recording. In an operational mode, the contacts are operated for signal stimulation only. In a configuration mode, the contacts may however also be controlled to operate in a signal recording modus such that neural activity or neural response to the stimulation signal may be recorded accordingly. In an example, each contact may be arranged such that is can operate both in the stimulation and recording modus, and in an alternative example, contacts may be dedicated for either signal stimulation or signal recording.

In order for the electrical contacts to process the signal for neural stimulation or neural recording, the system 100 consists of a driving unit and a recording unit. These units may be contained in separate housings, at separate locations in or on the patient, but are preferably contained in a transducer device which may be close to or integrated with the shaft or positioned directly under the scalp on the skull, for example in or near the layer of loose connective tissue of the scalp.

In order for flexible electrode shafts to successfully penetrate the surface tissue of the cerebral cortex, the system 100 also consists of a rigid electrode support structure. To this end, support structure consists of an array of rigid or stiff insert shafts. The flexible elongated electrode shafts are attached or fixed to the insert shafts of the support structure upon intracortical implantation in the cerebral cortex. Once inserted, the insert shafts disengage such that the insert shafts can be retracted, whereas the electrode shafts remain in place in the cerebral cortex. Attaching and disengaging can be achieved in different ways. For example, the inserts and respective electrodes may be temporarily attached by a brain fluid dissolvable adhesive such as PEG. This example may well work with flat ribbon shaped electrodes. In an alternative, non-flat shape of the ribbon, e.g. with a round or circular cross sectional shape, the tip of the electrode may be provided with an engaging element such as a hole that is to be penetrated by the tip of the insert shaft.

The electronics of the driving unit, to electrically drive the electrode unit for stimulation of the subset of locations, as well as the recording unit, to obtain neural recording through the electrode unit in the region of the cerebral cortex, can be packaged inside an implantable transducer casing 120 and shielded from the tissue by the material of the casing, which is preferably made of titanium. In case the electronics or electronic circuitry may reside on the electrode unit or more particular, on the three-dimensional arrays, they are embedded in a tissue compatible packaging material such as LCP or polyimide.

The implant 120 also consists of a switching unit. The switching unit consists of electronic circuitry which channels stimulation signals from the driving unit to the actual electrical contacts located in the cerebral cortex. What that means is, that the driving unit may be equipped with circuitry to generate a plural stimulation signal, i.e. a stimulation pulse of a particular waveform such as a sine wave form, a square wave form, a rectangular wave form, a triangular wave form, a sawtooth wave form, a pulse wave form or any combination of wave forms. The generated signals may not only differ in shape but also in amplitude and can be channelled to different individual or subsets of electrical contacts. This way some groups or subsets of contacts may not be activated at all, others with a first stimulation signal, yet another group with a second, different stimulation signal, and so on. To this end, the switching unit is arranged to achieve electrical channelling of the different signal generators and the subsets of electrical contacts.

To control the driving unit, the recording unit, and thereby the electrodes of the electrode unit, the system is also provided with a processing unit 170. The processing unit is preferably a handheld device, since that will increase independence and quality of life of the patient. The processing unit or device could be a general-purpose hand-held device, such as the mobile phone as shown by way of example in FIG. 1, which is programmed to operate as processing unit 170 for the neuroprosthetic system 200 according to the invention. The processing unit or device is however more preferably a dedicated device but with dimensions that are preferably similar to those of a mobile phone.

The processing unit 170 may communicate with the transducer arrangement or transducer device 120 by use of a wireless communication unit 110. This wireless communication unit 110 not only provides wireless technology to control high-channel-count high-density cortical implantable arrays 130a-130c, but also provides a wireless power transfer interface that can send the signals of the recording unit. This can be achieved for example through capacitive, or magnetodynamic, but preferably through inductive coupling between the wireless unit 110 and the transducer implant 120.

By having both wireless power and data communication between the wireless unit 110 and the transducer implant 120, the risk of infection that is associated with skin-penetrating cables and connectors is reduced.

With the processing unit 170, the system 100 is able to receive and analyse the data stream sensed by the sensor. In the example shown in FIG. 1, these are images of the data stream captured by the camera 150. These images have to be processed in such a way that the correct electrical contacts are powered or provided with a stimulation signal to evoke a phosphene, i.e. a phenomenon characterized by the experience of seeing light or a specific light dot, at a phosphene location which corresponds to the actual position of the electrode shaft or more precise, the electrical contact of that particular electrode shaft. The subset of phosphene locations should correspond to one or more objects that are captured by the camera and thus in the scene in the field of view 160 of the patient.

In order to make such a translation between actual captured image data and the subset of phosphene location, which together form a phosphene pattern or patterns, the processing unit 170 employs semantic segmentation.

With semantic segmentation, the image is processed such that each pixel is assigned to a particular object class. The object is in a way labelled and contains a set of pixels that enclose or outline the object.

Once the processing unit 170 processed the image data through semantic segmentation, an outline, contour, label, shape or other primitive object is determined which can then be used to as phosphene or stimulation pattern to apply stimulation signals to the appropriate subset of phosphene location. Once these stimulation signals are applied, the invoked phosphenes at these phosphene locations will substitute the visual perception of the patient such that he or she will recognize the actual object as a car or whatever object is in the field of view 160 of the patient In FIG. 2 an assembly 130 is shown of a three-dimensional array 133 of flexible, elongated electrodes or electrode shafts with a rigid electrode support structure 132 for guiding the flexible elongated electrodes 135 upon intracortical implantation in a region of the cerebral cortex of a patient.

The support structure 132 enables simultaneously guiding of the flexible electrode shafts 135 of the array 133 upon implementation and once implemented the insert shafts 134 may detach from the electrodes 135 and the support structure 132 can be retracted. All insert shafts 134, which preferably are manufactured from tungsten, are mutually connected and connected to a metal rod which makes simultaneous, concurrent insertion and retraction possible.

Figure 2:
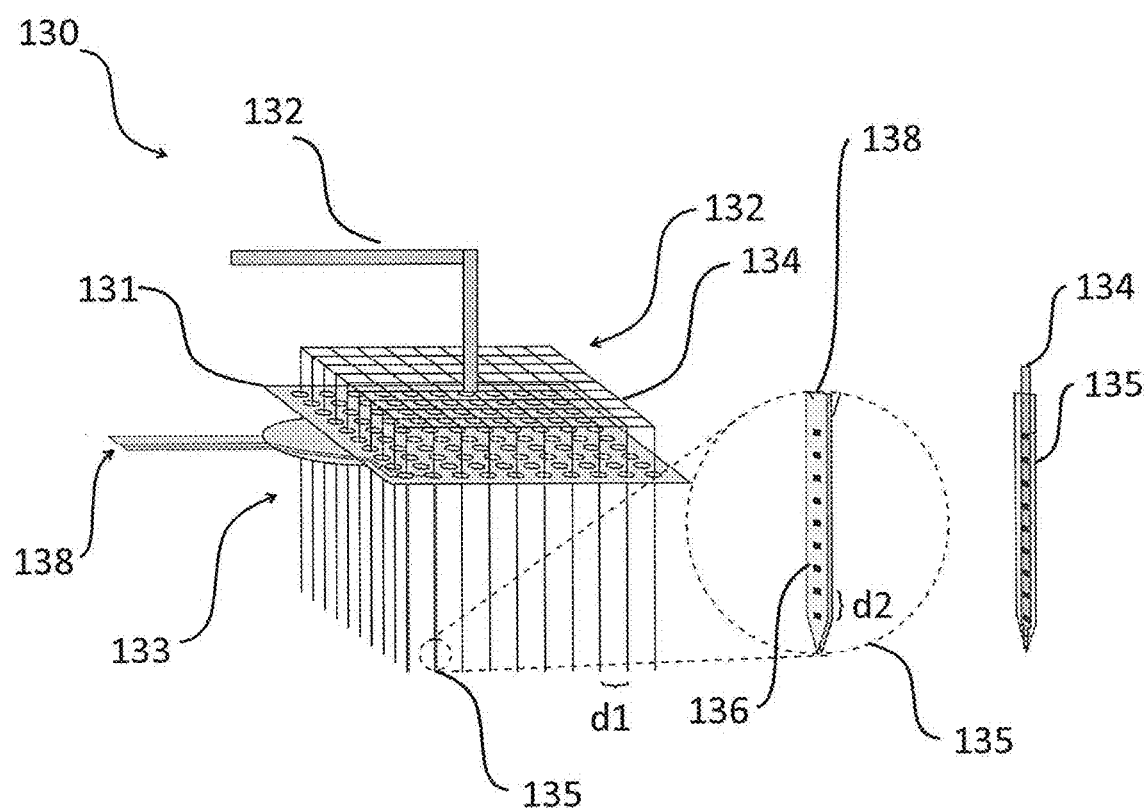
FIG. 2 illustrates an assembly of a three-dimensional array of electrodes and a support structure according to the present disclosure.

As clearly indicated in FIG. 2, both the number and the distribution of the insert shafts 134 of the support structure correspond to a number and distribution of through holes in the base plate 131 of the array 133, such that each individual insert shaft 134 is guided by a single respective though hole, thereby ensuring that all electrode shafts or electrode ribbons 135 arrive at the correct position and at the correct depth in the visual region of the cerebral cortex. This could preferably be primary cerebral region V1, but also mid-ranged or high regions such as V2, V3 or V4.

All individual electrodes 135 preferably have the same length of approximately 0.2-4 cm. The spacing between the individual electrodes is preferably approximately between 0.1 and 2 mm.

Each electrode shaft 135 contains multiple electrical contacts 136 which are distributed preferably in the longitudinal direction of the shaft. The contact 136 may however also have a lateral distribution pattern or could be distributed in both a lateral and longitudinal direction of the shaft.

Each electrical contact 136 is electrically wired through an electrical lead. The plurality of leads 138 are electrically connected to the transducer unit 120 as shown in FIG. 1.

As illustrated in the two detailed views in FIG. 2 there are several ways in which the electrode shafts 135 can engage with the insert shafts 134 of the support structure 132. In the example shown in the left detailed view the rigid insert shafts 134 have a rectangular cross section with a width that is identical or least approximately identical to the electrode shaft 135. The thickness in that particular example is in the range of 10-50 μm. In this example, it is preferred to use a dissolvable material such as PEG.

In the example shown in the right detailed view the rigid insert shafts 134 may or may not have a circular cross-section with a diameter of approximately 10-50 μm. In this example, the insert shafts 134 have a tapered or smaller diameter tip or free end to engage with a hole in the tip or free end of the electrode shaft 135.

Although the right detailed view might suggest that the electrical contacts are located on the insert shafts 134, they are actually located on the electrode shaft 135. The electrode shafts 134 can be sleeve shaped to receive the insert shafts 134, but these are more preferably flat opaque ribbon shaped electrodes with a through hole or other receiving element to receive the tip of the insert shaft for ease of surgical insertion into the brain.

In this example, there is no need for a dissolvable material such as PEG. Once the electrode shafts 135 are in position, the rigid insert shafts can easily be retracted, leaving the electrodes 135 in place.

Figure 3:
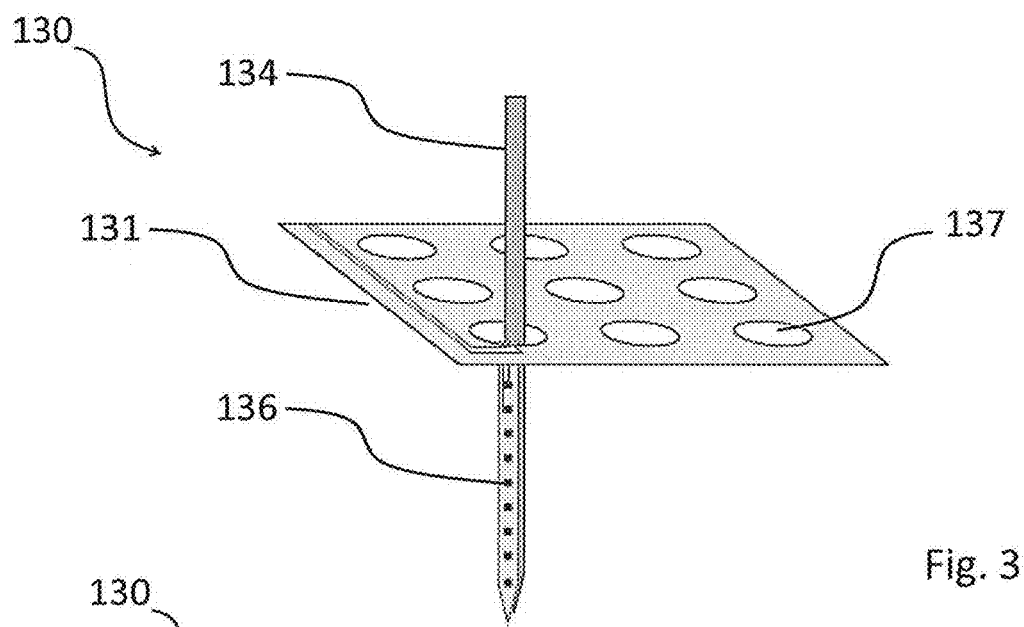
FIG. 3 illustrates a detailed view of an insert shaft of the support structure for inserting the electrode of the three-dimensional array according to the present disclosure.

FIG. 3 shows a more detailed view of the base plate 131 of the electrode array 133 with a two-dimensional distribution pattern of the through holes 137. FIG. 3 only shows one single electrode and insert shaft. The electrode unit and support structure will however contain a similar number of electrodes and insert shafts that correspond to the amount of through holes 137.

Figure 4:
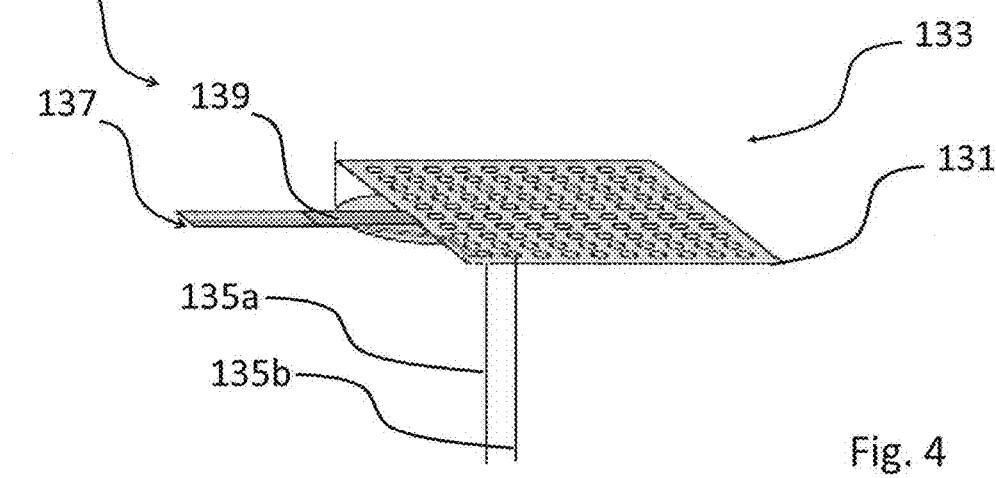
FIG. 4 illustrates the transducer unit and multiple three-dimensional arrays according to the present disclosure.

In FIG. 4 the electrode array 133 also contains additional circuitry 139 In one example of the invention all electrical contacts of each electrode shaft of each array are electrically wired to the transducer 120. In the example shown in FIG. 4 the array however comprises a multiplexer to multiplex and de-multiplex the signals of the large number of electrical wires 138 to one or more likely a lower number of wires. Since per insert, the number of wires could be as high as 50,000 the use of several multiplexers is desirable. The multiplexer may however be located either on the array 133, as shown in FIG. 4, or may also be located in the transducer 120.

Figure 5:
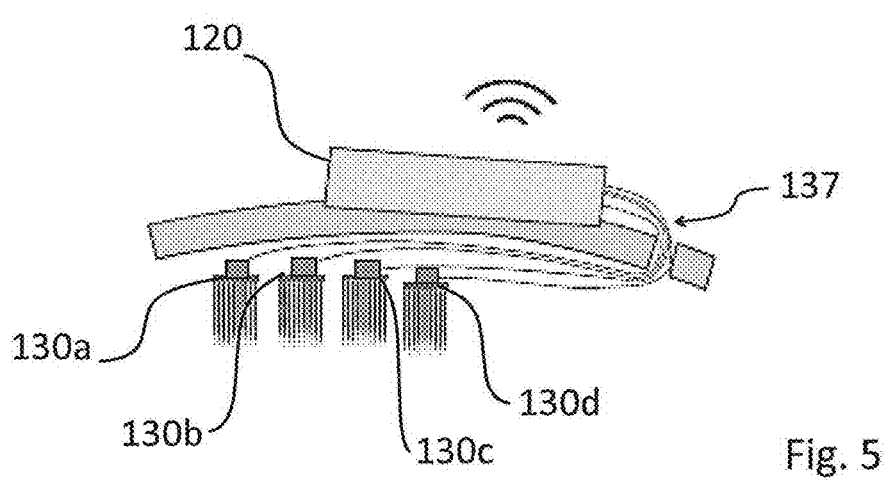
FIG. 5 illustrates the transducer unit and the lead connections to the arrays according to the present disclosure.

In FIG. 5 each array 130a-130d comprises a multiplexer 139. Although it might be preferable to have the multiplexers as near as possible to the huge number of wires, thus on or near the array, this would reduce the number and length of the leads or wires but could also produce too much heat that may affect the brain. In that case, it is preferred to have all wires run to the transducer and have them connected to multiplexers within the transducer casing 120.

Although the driving unit and the recording unit could also reside in each array 130, they are preferably located within the transducer unit 120. In the example shown in FIG. 4 however at least some electronic circuitry 139 is located on the array itself. In this example the electronic circuitry 139 may be arranged to multiplex the plurality of signals that are obtained in the recording modus through the large number of electrodes, but is preferably also arranged as switching unit to perform the channelling of the signal generators. Thus, to connect groups of electrical contacts with one of the signal generators.

Figure 6:
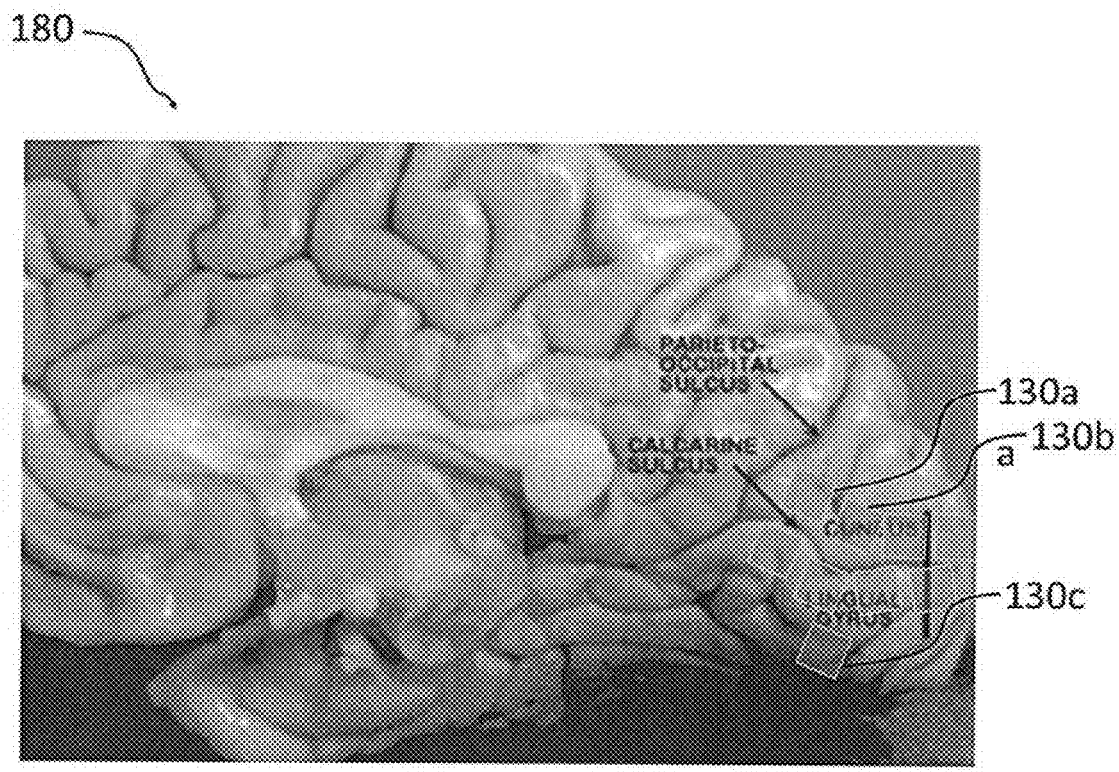
FIG. 6 illustrates a side view of a brain with multiple arrays in the visual region of the cerebral cortex according to the present disclosure.

FIG. 6 shows a side view of the brain 180 of the patient. In the example shown in FIG. 6, several arrays 130 are implanted the visual region of the cerebral cortex. Most of the arrays 130a, 130b etc. are implanted in area V1. However, at least one of the arrays 130c is however implanted to achieve at least partly or fully coverage of area V4, this in order to perform the recording and stimulation in such a higher visual cortex region.

As indicated above, this visual region is only an example in which the arrays according to the present disclosure can be implanted. Other sensory modality regions of the cerebral cortex may be implanted with similar arrays according to the present disclosure. These regions, such as the auditory regions or auditory cortex may for example be implanted with similar arrays which however have electrode shafts with different dimensions adapted to that particular region.

In view of the above, the skilled person will appreciate that the dimensions such as length of the electrode shafts as indicated relate in general to the visual cortex. Although these dimensions may very well also be suitable for other regions such as the auditory, tactile, somatosensory or olfactory functionality. Some or all of these regions may however require different dimensions.

Figure 7:
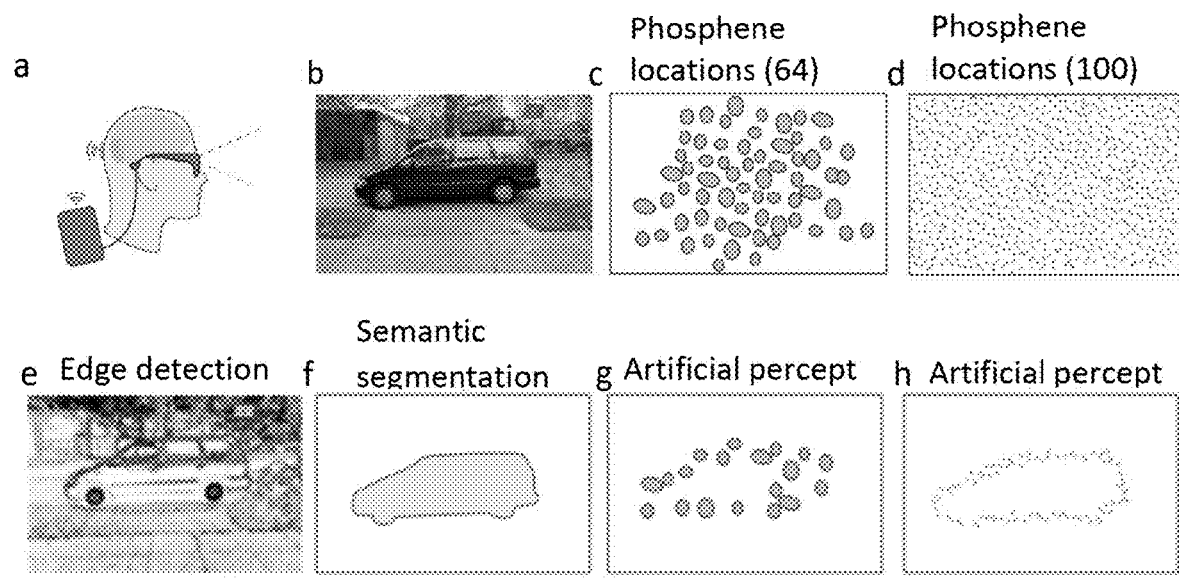
FIG. 7 illustrates several steps of semantic segmentation of an image captured by the camera of a system according to the present disclosure.

FIG. 7 shows several steps a-h of the translation of the images of the data stream feed into a phosphene pattern by making use of semantic segmentation. In step a, the camera images are electrically imparted to the retina or cortex using an image transformation algorithm in a portable device. In step b, an example is shown of an outdoor scene that is within the field of view of the patient shown in figure a. Imagine that the patient approaches the car. In step c, the locations of 64 phosphenes are shown that the patient can perceive when retinal electrodes are stimulated. Step d, shows the potential locations of 1,000 phosphenes that can be achieved by the stimulation of cortical area V1. In step e, a limitation of known prosthetic devices is shown which are not able to distinguish between relevant and irrelevant contours (such as foreground and background information in the image). Semantic segmentation algorithms however delineate the pixels in the image that belong to the car. The result of semantic segmentation as shown in step f, can be used as template to determine the stimulation patterns as shown in step g. If semantic segmentation is used to determine the pattern of activated phosphenes (subset of those in step c), perception of the approximate location and shape of the car is expected, resulting in a large improvement of vision through the prosthetic device. In step g, a cortical prosthesis according to an aspect of the invention can give rise to an even higher resolution percept.

Other variations to the disclosed examples can be understood and effected by those skilled in the art in practicing the claimed disclosure, from a study of the drawings, the disclosure and the appended claims. In the claims, the word "comprising" does not exclude other elements or steps and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as optical storage medium or a solid-state medium supplied together with or as part of other hardware, but may also be distributed in other forms, such as via the internet or other wired or wireless telecommunication systems. Any reference signs in the claims should not construed as limiting scope thereof. Similar reference signs denote similar or equivalent functionality.

The present disclosure is not limited to the examples as disclosed above, and can be modified and enhanced by those skilled in the art beyond the scope of the present disclosure as disclosed in the appended claims without having to apply inventive skills and for use in any data communication, data exchange and data processing environment, for example for use of the neuroprosthetic system for substituting auditory perception.

The invention claimed is:

1. A neuroprosthetic system for substituting a sensory modality of a mammal by electrical stimulation of a region of the cerebral cortex of the mammal corresponding to the sensory modality to be substituted, comprising:
   at least one sensor, for use by the mammal, for generating a sensed data feed by sensing a sensory modality to be substituted;
   an electrode unit, comprising a plurality of three-dimensional arrays of flexible electrode shafts, for intracortical implantation for an occupation of the region of the cerebral cortex of the mammal for providing functional coverage of the sensory modality, each flexible electrode shaft comprising multiple electrical contacts for electrical stimulation of subsets of locations in the region of the cerebral cortex;
   a rigid electrode support structure for simultaneously guiding the flexible electrode shafts of an array into the region of the cerebral cortex of the mammal during intracortical implantation, and for detaching from the array of flexible electrode shafts and retracting the rigid electrode support structure after implantation of the array of the flexible electrode shafts, the rigid electrode support structure including a plurality of rigid insert shafts, wherein each rigid insert shaft extends alongside and is removably attached to one of the flexible electrode shafts by a temporary interface configured to detach post-intracortical implantation;
   a driving unit for electrically driving the electrode unit for stimulating the subsets of locations in the region of the cerebral cortex;
   a recording unit for obtaining neural recording through the electrode unit in the region of the cerebral cortex; and
   a processing unit for analysing the sensed data feed for providing stimulation patterns for electrically driving groups of electrical contacts of the electrode unit corresponding to the subsets of locations in the region of the cerebral cortex, for substituting the sensory modality.

2. The neuroprosthetic system according to claim 1, wherein:
   the neuroprosthetic system is operable for substituting visual perception in a visual region of the cerebral cortex of the mammal;
   the at least one sensor comprises at least one portable imaging unit for capturing images and generating a captured image data feed;
   the driving unit is operable for evoking phosphenes at locations in the visual region of the cerebral cortex; and
   the processing unit is operable for providing the stimulation patterns for stimulating groups of electrical contacts of the electrode unit corresponding to subsets of phosphene locations in the visual region of the cerebral cortex for evoking phosphenes for substituting the visual perception comprised of phosphene patterns obtained through semantic segmentation of images of the captured image data feed.

3. The neuroprosthetic system according to claim 1, further comprising a switching device for channelling one or more stimulation signals of the driving unit to subsets of electrical contacts located within the region of the cerebral cortex providing the functional coverage of the sensory modality.

4. The neuroprosthetic system according to claim 1, wherein the processing unit is configured to determine correlations between neural signals from the electrodes, and locations in the region of the cerebral cortex, for deducing functional maps of the sensory cortex.

5. The neuroprosthetic system according to claim 1, wherein:
   the processing unit comprises a transceiver configured for wireless data communication;
   the neuroprosthetic system comprises a signal transducer arrangement configured for wireless data communication with the processing unit, the signal transducer arrangement configured for controlling the recording unit and the driving unit for driving and recording of the electrical contacts in a calibration mode and an operational mode, wherein the electrical contacts in the operational mode are controlled for signal stimulation and in the calibration mode for signal stimulation and signal reception, and wherein the signal transducer arrangement is configured for controlling the driving unit in the calibration mode for driving the electrical contacts for signal stimulation in the region of the cerebral cortex, and signal reception in one or more other cortex areas for determining potential locations in the region of the cerebral cortex for substituting the sensory modality.

6. The neuroprosthetic system according to claim 5, wherein the signal transducer arrangement is configured for controlling the driving unit in the calibration mode for driving the electrical contacts in one of signal stimulation and signal reception at predetermined regular time intervals, for recalibrating at least one of stimulation signals and potential locations in the region of the cerebral cortex for substituting the sensory modality.

7. The neuroprosthetic system according to claim 6, wherein the signal transducer arrangement comprises electrical simulation circuitry operable for simultaneously energizing, during the operational mode, a plurality of electrical contacts corresponding to the subsets of locations for substituting the sensory modality in accordance with sensory primitives.

8. The neuroprosthetic system according to claim 1, wherein the processing unit is configured for analysing the sensed data feed for providing the stimulation patterns based on convolutional neural networks.

9. The neuroprosthetic system according to claim 1, further comprising at least one eye-tracking sensor for sensing perceptual information for augmenting the substitution of the sensory modality.

* * * * *